United States Patent
Yoshida et al.

(10) Patent No.: US 10,274,459 B2
(45) Date of Patent: Apr. 30, 2019

(54) GENE MUTATION ANALYZER, GENE MUTATION ANALYSIS SYSTEM, AND GENE MUTATION ANALYSIS METHOD

(71) Applicant: Hitachi, Ltd., Chiyoda-ku, Tokyo (JP)

(72) Inventors: Makiko Yoshida, Tokyo (JP); Takahide Yokoi, Tokyo (JP); Takashi Anazawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 159 days.

(21) Appl. No.: 14/378,878

(22) PCT Filed: Jul. 31, 2013

(86) PCT No.: PCT/JP2013/070691
§ 371 (c)(1),
(2) Date: Aug. 14, 2014

(87) PCT Pub. No.: WO2015/015585
PCT Pub. Date: Feb. 5, 2015

(65) Prior Publication Data
US 2016/0187292 A1 Jun. 30, 2016

(51) Int. Cl.
*G01N 27/447* (2006.01)
*C12Q 1/6816* (2018.01)
(Continued)

(52) U.S. Cl.
CPC ..... *G01N 27/44704* (2013.01); *C12Q 1/6816* (2013.01); *C12Q 1/6825* (2013.01);
(Continued)

(58) Field of Classification Search
None
See application file for complete search history.

(56) References Cited

U.S. PATENT DOCUMENTS 5,821,058 A * 10/1998 Smith .................. C12Q 1/6816
435/6.12
7,660,676 B2  2/2010 Hirata et al.
(Continued)

FOREIGN PATENT DOCUMENTS

JP    5-219995 A    8/1993
JP    2002-55080 A  2/2002
(Continued)

*Primary Examiner* — Joseph Woitach
(74) *Attorney, Agent, or Firm* — Crowell & Moring LLP

(57) ABSTRACT

An aspect of the present invention includes performing electrophoresis of a nucleic acid sample to be analyzed labeled for each base type, generating waveform data of detected intensity by detecting a label signal for the each base type, selecting another peak position for each peak position of the waveform data for each base type, calculating relative signal intensity of signal intensity in each position relative to the signal intensity in the other selected position, and analyzing existence of each base type in a base sequence coordinate position of the nucleic acid sample by comparing the relative signal intensity of the nucleic acid sample to be analyzed and the relative signal intensity of a known nucleic acid sample in each peak position. Accordingly, acquiring information about a gene mutation in trace amounts existing in a target gene region highly sensitively with high precision is realized.

5 Claims, 11 Drawing Sheets

[GENE XX]

| BASE SEQUENCE | A | G | T | C | A | G | T | C |
|---|---|---|---|---|---|---|---|---|
| A ratio | 95 | 10 | 5 | 0 | 90 | 0 | 0 | 0 |
| G ratio | 5 | 90 | 0 | 0 | 5 | 100 | 0 | 0 |
| C ratio | 0 | 0 | 95 | 0 | 5 | 0 | 100 | 0 |
| T ratio | 0 | 0 | 0 | 100 | 0 | 0 | 0 | 100 |

12a, 12b, 12c, 12d, 12e

(51) Int. Cl.
*C12Q 1/6825* (2018.01)
*G01N 30/88* (2006.01)

(52) U.S. Cl.
CPC . G01N 27/44726 (2013.01); G01N 27/44791 (2013.01); *G01N 2030/8827* (2013.01)

(56) References Cited

U.S. PATENT DOCUMENTS

2002/0090630 A1   7/2002  Hazama
2003/0224395 A1* 12/2003  Jovanovich .......... C12Q 1/6869
                                            506/16
2004/0110137 A1   6/2004  Hirata et al.

FOREIGN PATENT DOCUMENTS

| JP | 2002-78500 A   | 3/2002 |
| JP | 2002-168868 A  | 6/2002 |
| JP | 2003-270206 A  | 9/2003 |
| JP | 2004-187545 A  | 7/2004 |
| JP | 2004-208650 A  | 7/2004 |
| JP | 2005-31051 A   | 2/2005 |

* cited by examiner

FIG. 6

[GENE XX]

BASE TYPE A — 601

| POSITION | KNOWN SEQUENCE | $I_1$ | | $I_2$ | | $I_3$ | | $I_4$ | | $I_5$ | |
|---|---|---|---|---|---|---|---|---|---|---|---|
| | | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION |
| . | . | ... | ... | ... | ... | ... | ... | ... | ... | ... | ... |
| 99 | T | 0.048 | 0.011 | 1.02 | 0.011 | 0.81 | 0.014 | 1.15 | 0.028 | 0.93 | 0.014 |
| 100 | C | 0.061 | 0.016 | 0.91 | 0.025 | 0.72 | 0.019 | 0.92 | 0.022 | 1.06 | 0.020 |
| 101 | G | 0.087 | 0.017 | 0.87 | 0.022 | 1.02 | 0.023 | 0.94 | 0.014 | 1.05 | 0.021 |
| . | . | ... | ... | ... | ... | ... | ... | ... | ... | ... | ... |

BASE TYPE G — 602

| POSITION | KNOWN SEQUENCE | $I_1$ | | $I_2$ | | $I_3$ | | $I_4$ | | $I_5$ | |
|---|---|---|---|---|---|---|---|---|---|---|---|
| | | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION |
| . | . | ... | ... | ... | ... | ... | ... | ... | ... | ... | ... |
| 99 | T | 0.063 | 0.007 | 0.97 | 0.014 | 0.87 | 0.018 | 1.21 | 0.028 | 0.79 | 0.011 |
| 100 | C | 0.035 | 0.013 | 1.02 | 0.015 | 0.97 | 0.013 | 0.87 | 0.014 | 0.99 | 0.021 |
| 101 | G | 0.98 | 0.021 | 1.11 | 0.017 | 1.04 | 0.017 | 0.83 | 0.009 | 1.07 | 0.019 |
| . | . | ... | ... | ... | ... | ... | ... | ... | ... | ... | ... |

BASE TYPE C — 603

| POSITION | KNOWN SEQUENCE | $I_1$ | | $I_2$ | | $I_3$ | | $I_4$ | | $I_5$ | |
|---|---|---|---|---|---|---|---|---|---|---|---|
| | | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION |
| . | . | ... | ... | ... | ... | ... | ... | ... | ... | ... | ... |
| 99 | T | 0.077 | 0.010 | 0.85 | 0.021 | 1.18 | 0.018 | 0.87 | 0.020 | 1.17 | 0.017 |
| 100 | C | 1.15 | 0.021 | 0.91 | 0.025 | 0.72 | 0.019 | 0.92 | 0.022 | 1.06 | 0.020 |
| 101 | G | 0.057 | 0.013 | 0.77 | 0.013 | 0.99 | 0.021 | 1.07 | 0.021 | 1.01 | 0.014 |
| . | . | ... | ... | ... | ... | ... | ... | ... | ... | ... | ... |

BASE TYPE T — 604

| POSITION | KNOWN SEQUENCE | $I_1$ | | $I_2$ | | $I_3$ | | $I_4$ | | $I_5$ | |
|---|---|---|---|---|---|---|---|---|---|---|---|
| | | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION | AVERAGE VALUE | STANDARD DEVIATION |
| . | . | ... | ... | ... | ... | ... | ... | ... | ... | ... | ... |
| 99 | T | 0.94 | 0.021 | 0.82 | 0.014 | 1.19 | 0.024 | 1.21 | 0.019 | 0.97 | 0.014 |
| 100 | C | 0.061 | 0.016 | 0.91 | 0.025 | 0.72 | 0.019 | 0.92 | 0.022 | 1.06 | 0.020 |
| 101 | G | 0.072 | 0.011 | 1.18 | 0.021 | 1.07 | 0.020 | 0.99 | 0.015 | 0.91 | 0.018 |
| . | . | ... | ... | ... | ... | ... | ... | ... | ... | ... | ... |

FIG. 11

[GENE XX]

BASE TYPE A — 1101

| POSITION | KNOWN SEQUENCE | REGRESSION EQUATION $I_I = a(R - \mathrm{Mean}(R)) + \mathrm{Mean}(I_I)$ | | | |
|---|---|---|---|---|---|
| | | INCLINATION a | AVERAGE VALUE OF ABUNDANCE RATIO Mean(R) | AVERAGE VALUE OF RELATIVE INTENSITY Mean($I_I$) | STANDARD DEVIATION $\sigma^2$ |
| . | . | ... | ... | ... | ... |
| 99 | T | 0.011353 | 0.5 | 0.448 | 0.000490 |
| 100 | C | 0.012494 | 0.5 | 0.461 | 0.000341 |
| 101 | G | 0.011245 | 0.5 | 0.487 | 0.000791 |
| . | . | ... | ... | ... | ... |

BASE TYPE G — 1102

| POSITION | KNOWN SEQUENCE | REGRESSION EQUATION $I_I = a(R - \mathrm{Mean}(R)) + \mathrm{Mean}(I_I)$ | | | |
|---|---|---|---|---|---|
| | | INCLINATION a | AVERAGE VALUE OF ABUNDANCE RATIO Mean(R) | AVERAGE VALUE OF RELATIVE INTENSITY Mean($I_I$) | STANDARD DEVIATION $\sigma^2$ |
| . | . | ... | ... | ... | ... |
| 99 | T | 0.009255 | 0.5 | 0.463 | 0.000320 |
| 100 | C | 0.012134 | 0.5 | 0.435 | 0.000411 |
| 101 | G | 0.010342 | 0.5 | 0.498 | 0.000573 |
| . | . | ... | ... | ... | ... |

BASE TYPE C — 1103

| POSITION | KNOWN SEQUENCE | REGRESSION EQUATION $I_I = a(R - \mathrm{Mean}(R)) + \mathrm{Mean}(I_I)$ | | | |
|---|---|---|---|---|---|
| | | INCLINATION a | AVERAGE VALUE OF ABUNDANCE RATIO Mean(R) | AVERAGE VALUE OF RELATIVE INTENSITY Mean($I_I$) | STANDARD DEVIATION $\sigma^2$ |
| . | . | ... | ... | ... | ... |
| 99 | T | 0.011984 | 0.5 | 0.477 | 0.000380 |
| 100 | C | 0.011824 | 0.5 | 0.415 | 0.000632 |
| 101 | G | 0.012412 | 0.5 | 0.457 | 0.000471 |
| . | . | ... | ... | ... | ... |

BASE TYPE T — 1104

| POSITION | KNOWN SEQUENCE | REGRESSION EQUATION $I_I = a(R - \mathrm{Mean}(R)) + \mathrm{Mean}(I_I)$ | | | |
|---|---|---|---|---|---|
| | | INCLINATION a | AVERAGE VALUE OF ABUNDANCE RATIO Mean(R) | AVERAGE VALUE OF RELATIVE INTENSITY Mean($I_I$) | STANDARD DEVIATION $\sigma^2$ |
| . | . | ... | ... | ... | ... |
| 99 | T | 0.012431 | 0.5 | 0.494 | 0.000482 |
| 100 | C | 0.009173 | 0.5 | 0.461 | 0.000634 |
| 101 | G | 0.011624 | 0.5 | 0.472 | 0.000571 |
| . | . | ... | ... | ... | ... |

FIG. 12

| [GENE XX] | | | | | | | | |
|---|---|---|---|---|---|---|---|---|
| BASE SEQUENCE | A | G | T | C | A | G | T | C |
| A ratio | 95 | 10 | 5 | 0 | 90 | 0 | 0 | 0 |
| G ratio | 5 | 90 | 0 | 0 | 5 | 100 | 0 | 0 |
| C ratio | 0 | 0 | 95 | 0 | 5 | 0 | 100 | 0 |
| T ratio | 0 | 0 | 0 | 100 | 0 | 0 | 0 | 100 |

12a — [GENE XX] / BASE SEQUENCE row
12b — A ratio
12c — G ratio
12d — C ratio
12e — T ratio

GENE MUTATION ANALYZER, GENE MUTATION ANALYSIS SYSTEM, AND GENE MUTATION ANALYSIS METHOD

TECHNICAL FIELD

The present invention relates to an analysis method of a gene mutation and an analyzer and an analysis system of a gene mutation. In particular, the present invention relates to an analyzer that analyzes the existence of each base type in a base sequence coordinate position of a nucleic acid sample by interpreting fluorescence intensity waveform data obtained from the nucleic acid sample of a target gene, an analysis system, and an analysis method.

BACKGROUND ART

As a method of decoding a DNA base sequence, DNA sequencing combining the fragmentation technology of a nucleic acid using the Sanger's method, the fluorescence labeling technology of nucleic acid fragments, the high-resolution electrophoretic technology, and further the sensitive fluorescence detection technology is widely used.

According to the DNA sequencing, DNA (template DNA) whose base sequence should be decoded is first prepared and a replication reaction of the template DNA is caused using a primer having a sequence complementary to a sequence of a portion of the template DNA. At this point, if dideoxynucleotide as chain termination nucleotide is mixed in a predetermined proportion in a reaction solution together with deoxynucleotide, the synthetic reaction stops in a position where dideoxynucleotide is incorporated and thus, nucleic acid fragments of various lengths can be generated. If the primer or dideoxynucleotide is labeled with fluorescent dyes of different colors for each base type, each nucleic acid fragment is labeled with the dye corresponding to the terminal base thereof. Nucleic acid fragments created in this manner are separated based on the base length by electrophoresis using a capillary electrophoretic device or the like. Each nucleic acid fragment is irradiated with laser at the end of electrophoresis to measure fluorescence emitted from the terminal base of each fragment by a detector. A shorter nucleic acid fragment moves faster in electrophoresis and thus, fluorescence intensity waveform data corresponding to the base sequence is obtained as chronological fluorescence measured data.

A DNA sequencer using the DNA sequencing is an apparatus that determines the base sequence by comparing intensity of four types of fluorescent signals in each peak position of the fluorescence intensity waveform data.

A gene mutation called single nucleotide polymorphism is known to exist in base sequences of genome of human beings and the like. A congenital gene mutation inheritable from parents to children is called a germline mutation. The genome of many living beings including human beings is constituted as diploid and thus, concerning a germline mutation, two bases exist in individuals or cells in the proportion of 50% respectively. When a region in which such single nucleotide polymorphism exists is analyzed by the DNA sequencer, fluorescent signal peaks corresponding to two bases are detected simultaneously in positions corresponding to the single nucleotide polymorphism of the fluorescence intensity waveform data.

According to the aforementioned sequencing, however, fluorescence intensity waveform data that makes the determination of the polymorphism or the determination of the base sequence difficult may be obtained. A case when the amount of nucleic acid sample is small and signal intensity is weak, a case when excessive signal components are generated due to a higher-order structure of nucleic acid fragments, or a case when signals are distorted by conditions during chemical treatment or electrophoresis can be considered as the cause thereof.

When the base sequence of an actual nucleic acid sample is determined, like when a certain gene is examined for a gene mutation, at least a portion of the base sequence of the nucleic acid sample is often known. When such a known base sequence exists, newly acquired fluorescence intensity waveform data can be interpreted by referring to information of fluorescence intensity waveform data obtained from the known base sequence by some method. When such a known base sequence exists, as disclosed by PTL 1 and PTL 2, newly acquired fluorescence intensity waveform data can be interpreted by referring to information of fluorescence intensity waveform data obtained from the known base sequence by some method.

CITATION LIST

Patent Literature

PTL 1: JP 2002-055080 A
PTL 2: JP 2005-031051 A

SUMMARY OF INVENTION

Technical Problem

With the development of genome analysis technology in recent years, correlations between various diseases of human beings and gene mutations have been clarified and pharmaceutical products have been developed by making use of genetic information. For example, a gene mutation is a factor of the onset of cancer and genetic tests of individual patients are already covered by insurance for the selection of a portion of therapeutic drugs or the determination of the quantity prescribed.

In contrast to the aforementioned germline mutation, an acquired gene mutation derived from a disease such as cancer is called a somatic mutation. The somatic mutation is characterized in that a mutation occurrence position on a genome cannot be predicted and a mutation abundance ratio in an individual or a tissue cannot be predicted. For example, a cancer tissue sample excised from a cancer patient contains cancer cells and normal cells and further, cancer cells contain a variety of gene mutations and therefore, the abundance ratio of cells having a gene mutation in a certain position of a certain gene in the sample may be very low. Therefore, to detect a somatic mutation, a more sensitive detection method than that of a germline mutation is needed.

When selecting the therapy or therapeutic drugs, not only the presence/absence of a gene mutation in a certain position of a target gene, but also its abundance ratio may also be taken as a guide. Thus, in addition to sensitive detection of a gene mutation, quantitation of its abundance ratio is also important. A conventional DNA sequencer using the Sanger's method is intended for the determination of a base sequence and so its enormous challenge has been that detection power of a somatic gene mutation that exists in trace amounts is insufficient and its abundance ratio cannot be quantified.

Further, a DNA methylation modification is known as a kind of genetic phenotypic variation that is not accompanied by a mutation of the base sequence and the DNA methylation modification state is known to change with the development/differentiation of cells or canceration of cells. Therefore, a method of easily detecting a methylation modified position of a base sequence and its modification ratio is expected.

PTL 1 described above presents a method of performing a normalization process on signal intensity in each peak position of fluorescence intensity waveform data by using signal intensity of the base type having the maximum signal intensity in the relevant peak position as the normalization reference when a polymorphism determination is made and the base sequence is determined. According to the normalization method, if a mutation exists in the relevant position and its abundance ratio is not constant, quantitative properties of signal intensity of each base type cannot be maintained.

PTL 2 described above presents a method of performing a normalization process on signal intensity of fluorescence intensity waveform data by using the average intensity of all peaks in the fluorescence intensity waveform data as the normalization reference. However, the peak intensity in the fluorescence intensity waveform data varies in the whole waveform data and the state of variations is different from data to data. Therefore, according to the normalization method using the average intensity of all peaks as a reference, the precision of normalization of signal intensity of individual peaks is insufficient. PTL is intended to determine main base sequences and the precision of normalization does not pose a big problem, but when the detection of a gene mutation or the determination of its abundance ratio is intended, insufficient precision of normalization could cause lower detection sensitivity or deterioration of determination precision.

In view of the above problems of conventional technology, an object of the present invention is to obtain information about a gene mutation highly sensitively with high precision even if the gene mutation is a somatic gene mutation existing in trace amounts.

Solution to Problem

An aspect of the present invention to solve at least one of the above problems includes performing electrophoresis of a nucleic acid sample to be analyzed labeled for each base type, generating waveform data of detected intensity by detecting a label signal for the each base type, selecting another peak position for each peak position of the waveform data for each base type, calculating relative signal intensity of signal intensity in each position relative to the signal intensity in the other selected position, and analyzing existence of each base type in a base sequence coordinate position of the nucleic acid sample by comparing the relative signal intensity of the nucleic acid sample to be analyzed and the relative signal intensity of a known nucleic acid sample in each peak position.

Advantageous Effects of Invention

According to the present invention, acquiring information about a gene mutation in trace amounts existing in a target gene region highly sensitively with high precision is realized.

BRIEF DESCRIPTION OF DRAWINGS

FIG. 6 is a diagram showing an example of the relative signal intensity information to detect a gene mutation stored in a known information database.

FIG. 11 is a diagram showing an example of the relative signal intensity information to estimate the gene mutation abundance ratio stored in the known information database.

FIG. 12 is a diagram showing a display example of gene mutation abundance ratio information according to the present invention.

DESCRIPTION OF EMBODIMENT

An embodiment of the present invention will be described below with reference to the drawings. However, the present embodiment is only an example to realize the present invention and does not limit the present invention.

Figure 1:
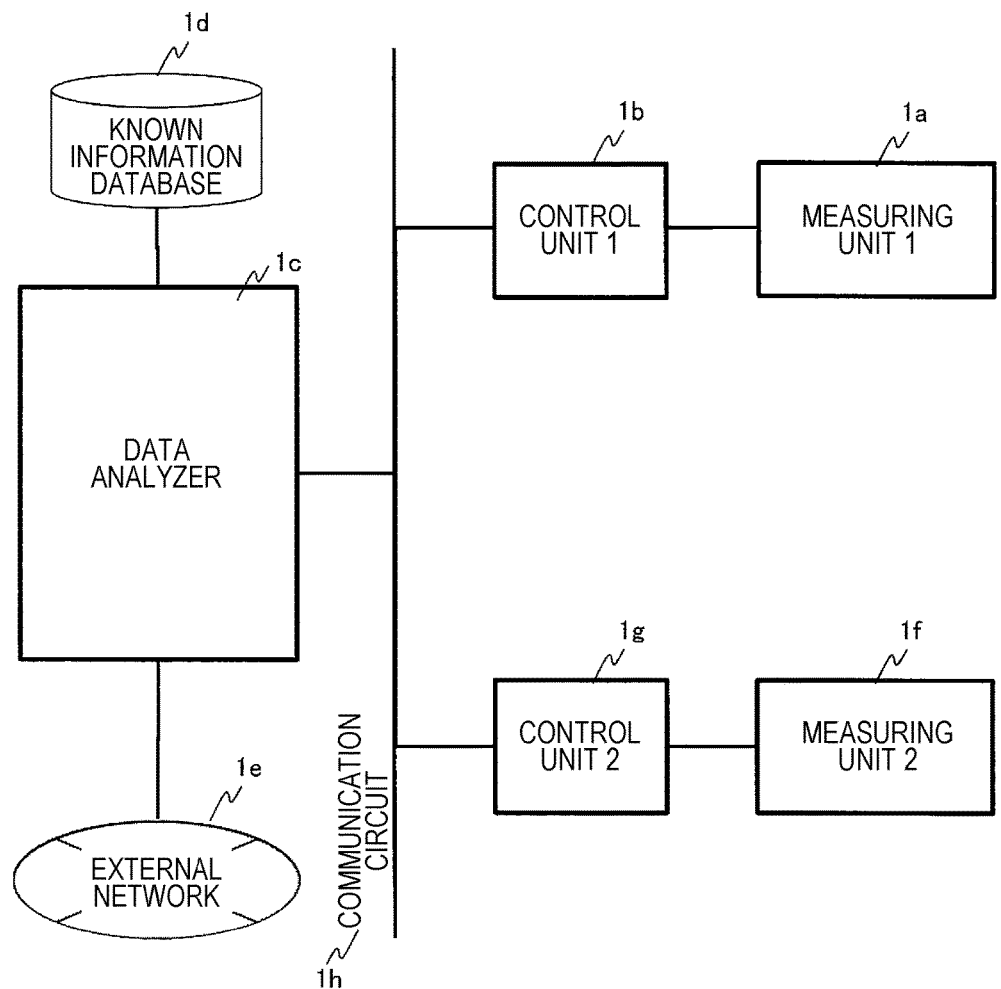
FIG. 1 is a diagram showing a configuration example of a gene mutation analysis system to which the present invention is applied.

FIG. 1 shows a configuration example of a gene mutation analysis system according to the present embodiment. The system includes fluorescence intensity waveform data measuring units 1a, 1f, control units 1b, 1g, a fluorescence intensity waveform data analyzer 1c, and a known information database 1d.

Figure 2:
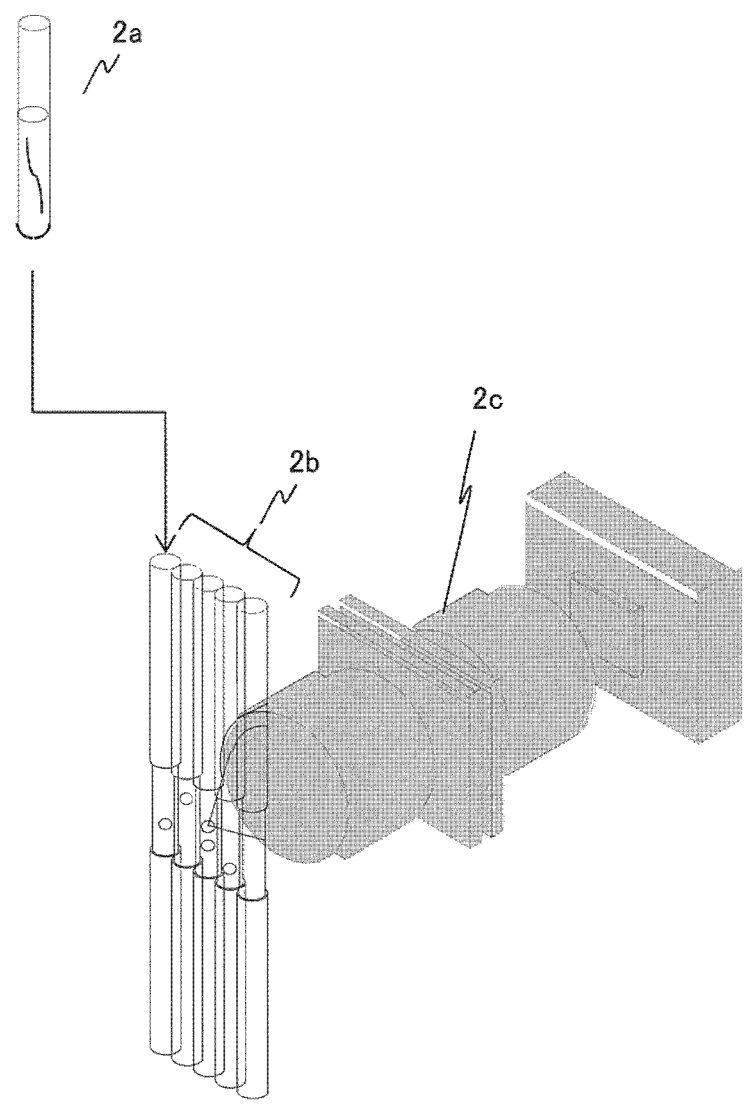
FIG. 2 is a diagram showing an example of a measuring unit of a gene mutation analyzer.

FIG. 2 shows a configuration example of the fluorescence intensity waveform data measuring units 1a, 1f. The fluorescence intensity waveform data measuring units 1a, 1f include a channel (2b) in which electrophoresis of a nucleic acid fragment in a nucleic acid sample (2a) labeled with fluorescent dyes is performed and a detector (2c) that chronologically detects fluorescence intensity.

The fluorescence intensity waveform data measuring units 1a, 1f acquire fluorescence intensity waveform data by performing electrophoresis in the channel (2b) of nucleic acid fragments labeled with fluorescence through the detector (2c). In this case, fluorescence intensity waveform data of each base type may separately be acquired by performing electrophoresis for each fluorescent dye or fluorescence intensity waveform data of four base types may be acquired simultaneously by performing electrophoresis after four types of fluorescent dyes being mixed.

The fluorescence intensity waveform data analyzer 1c determines the base sequence or detects or quantifies a mutation by performing signal processing of fluorescence intensity waveform data. Each function of the fluorescence intensity waveform data analyzer 1c described later using FIGS. 3, 5, 7, 8, 10, and 11 can be realized by each program realizing each function and stored in a memory being interpreted and executed by a processor inside the function of the fluorescence intensity waveform data analyzer 1c. Each function of the fluorescence intensity waveform data analyzer 1c, a processing unit, a processing means and the like may be realized by hardware by designing a portion or all thereof using, for example, an integrated circuit. Information of programs, files, databases and the like to realize each function can be placed in, for example, a recording apparatus such as a memory, a hard disk, an SSD (Solid State Drive) and the like or a recording medium such as an IC card, an SD card, DVD and the like.

The known information database 1d stores information related to base sequences and corresponding fluorescence intensity waveform data. The control units 1b, 1g control data transfer between each of units, measurements made by the fluorescence intensity waveform data measuring units 1a, 1f, and analysis processing content of the fluorescence intensity waveform data analyzer 1c. Further, the control units 1b, 1g can also transmit information used for analysis or analysis results by connecting to the external network 1e.

Figure 9:
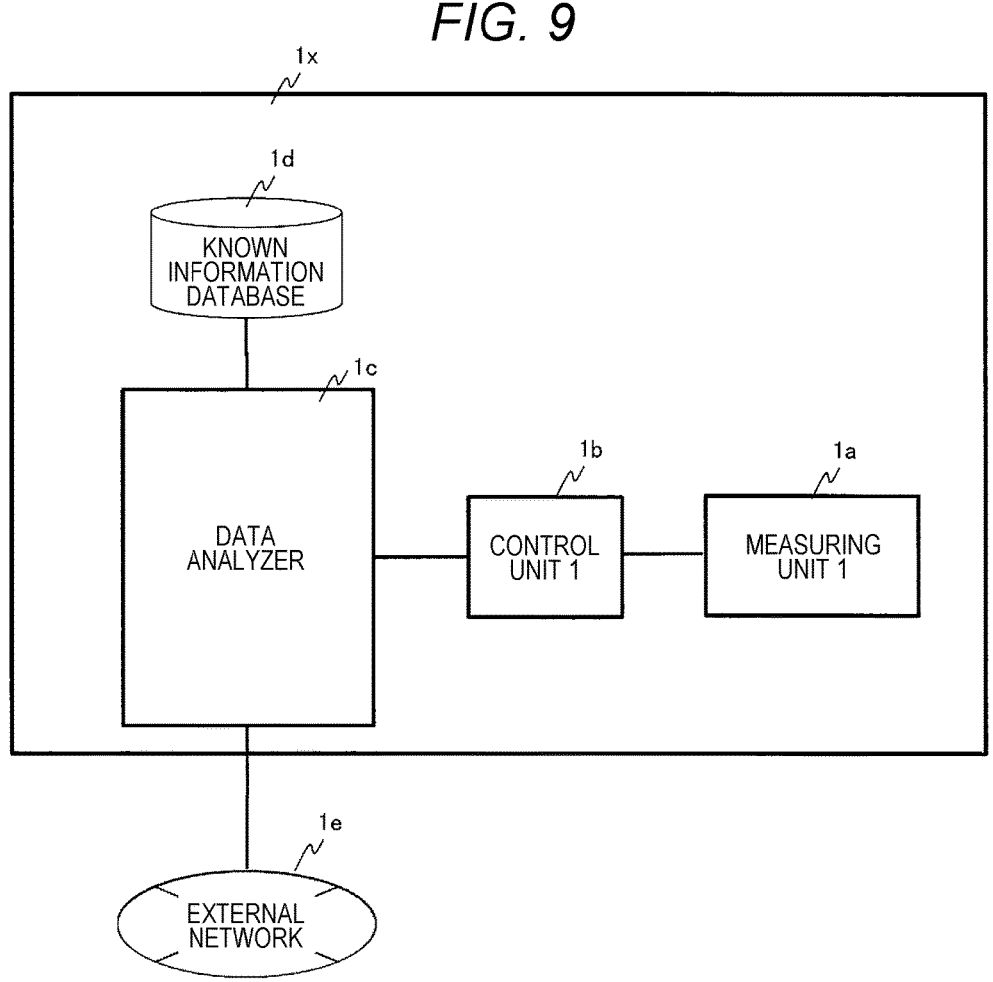
FIG. 9 is a diagram showing a configuration example of the gene mutation analyzer to which the present invention is applied.

FIG. 1 shows a system configuration in which the fluorescence intensity waveform data analyzer 1c as an analyzer is connected to the fluorescence intensity waveform data measuring units 1a, 1f as measuring devices via the control units 1b, 1g as control devices and also connected to the known information database 1d to acquire data by referring to the database, but as shown in FIG. 9, the system configuration can also be carried out as a gene mutation analyzer 1x including the fluorescence intensity waveform data measuring unit 1a, the control unit 1b, the fluorescence intensity waveform data analyzer 1c, and the known information database 1d.

Figure 3:
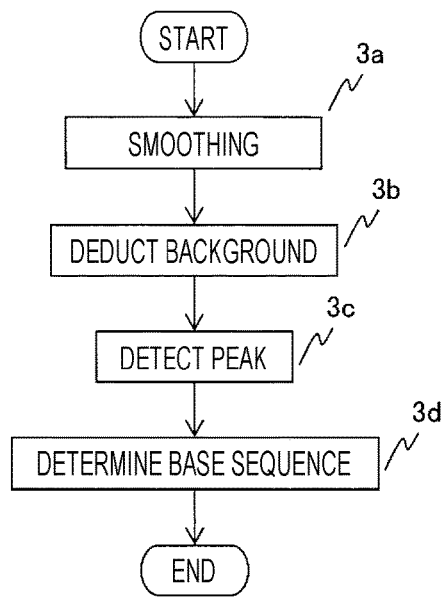
FIG. 3 is a diagram showing processing performed on fluorescence intensity waveform data when a base sequence is determined.

FIG. 3 is a flow chart of processing performed on fluorescence intensity waveform data when the fluorescence intensity waveform data analyzer 1c in FIG. 1 determines the base sequence of a nucleic acid sample. First, smoothing processing (3a) and background deduction processing (3b) are performed on the fluorescence intensity waveform data. Then, peaks are detected (3c) and the signal intensity in each position is extracted. Lastly, the base type is determined one after another by comparing signal intensity of four base types in each position and determining main signals based on predetermined criteria (3d).

Figure 4:
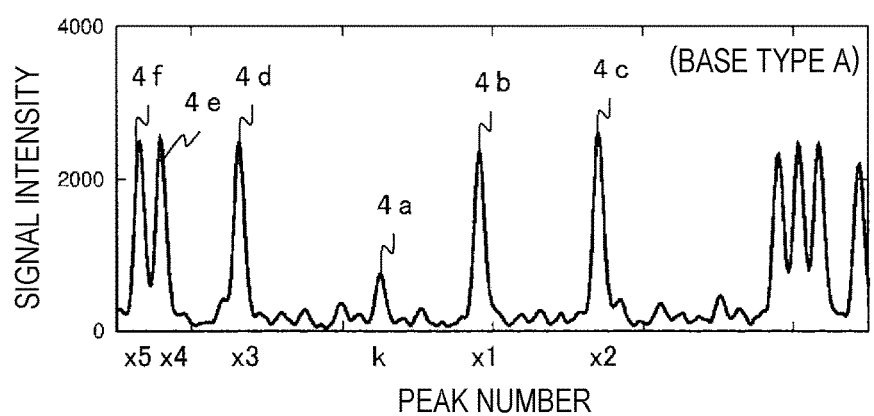
FIG. 4 is a diagram showing an example of the fluorescence intensity waveform data.

FIG. 4 shows an example of the fluorescence intensity waveform data of some base type. Because the data contains noise, signal intensity is extracted not only from positions corresponding to the relevant base type, but also from positions corresponding to other base types. In FIG. 4, sharp peaks are extracted from peak positions (for example, peak positions x1, x2, x3, x4, x5) corresponding to the relevant base type and a small signal derived from a mutation is extracted, in addition to noise signals, from a peak position (for example, a peak position k) where a minor mutation of the base type exists. In the present embodiment, the fluorescence intensity waveform data analyzer 1c in FIG. 1 has the function, in addition to the processing to determine the above base sequence in FIG. 3, to determine whether each base type exists in the base sequence coordinate position by taking relative signal intensity information of signal intensity in each peak position acquired from fluorescence intensity waveform data obtained for a known base sequence relative to signal intensity in other peak positions as a guide. As a concrete configuration example of the present embodiment that determines whether each base type exists in the base sequence coordinate position based on the relative signal intensity information, the function of detecting a gene mutation in each sequence coordinate position and the function of detecting the abundance ratio of each base type in each sequence coordinate position will be described in detail below.

<First Embodiment>

Figure 5:
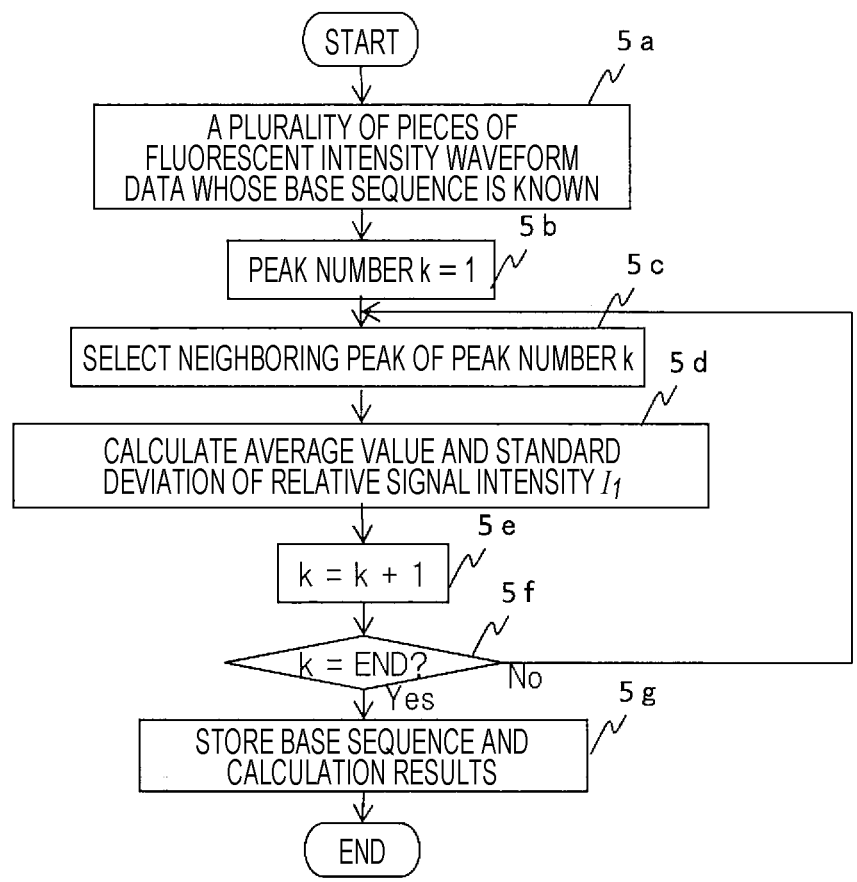
FIG. 5 is a diagram showing an example of processing that acquires relative signal intensity information to detect a gene mutation.
Figure 7:
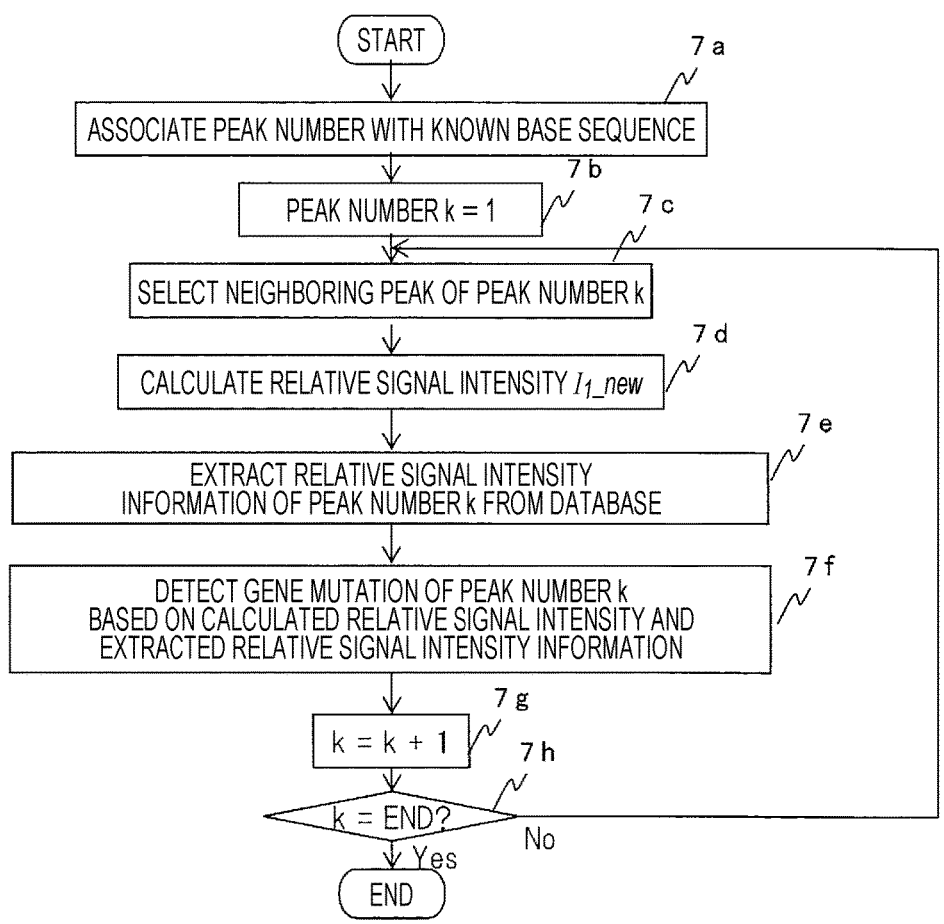
FIG. 7 is a diagram showing an example of detection processing of a gene mutation in the present invention.

In the present embodiment, as a more concrete configuration example of the present embodiment that determines whether each base type in the base sequence coordinate position exists based on relative signal intensity information of signal intensity in each peak position relative to signal intensity in other peak positions, an example of analysis processing that detects a gene mutation in fluorescence intensity waveform data performed by the fluorescence intensity waveform data analyzer 1c will be described using FIGS. 5, 6, and 7.

First, an example of processing in which the data analyzer 1c acquires relative signal intensity information for reference, that is, an example of processing that acquires relative signal intensity information from fluorescence intensity waveform data of the base type obtained for a known base sequence will be described using FIG. 5. It is assumed here that the waveform of the fluorescence intensity waveform data shown in FIG. 4 corresponds to a known base sequence to describe peak positions and the like.

In the processing in FIG. 5, a set of a plurality of pieces fluorescence intensity waveform data of some base type obtained for a known base sequence is prepared (5a). Based on the data set, in some peak position, a peak (peak number x1; 4b) that is a neighboring peak of the base type to the peak (peak number k; 4a) is selected (5b, 5c). Next, an average value and a standard deviation of relative signal intensity $I_1$ of the signal intensity I(k) in the peak position relative to the signal intensity I(x1) in the neighboring peak position in the data set are calculated (5d). The relative signal intensity $I_1$ is calculated by the following formula (1):

$$I_1 = I(k)/I(x1) \quad (1)$$

In the same manner as the above series of procedures, the average value and standard deviation of the relative signal intensity $I_1$ in the data set are calculated one by one for all positions (5e, 5f) and the base sequence and calculation results are stored in the known information database 1d (5g). The same processing is repeated for all base types.

For the relative signal intensity information, other peaks than the neighboring peak of the relevant peak may be selected or the other preset peak may be used for calculation. For example, a peak that decreases the standard deviation of relative signal intensity for some position may be selected.

The relative signal intensity information may be calculated not only for $I_1$ described above, but also a plurality of pieces of relative signal intensity may be calculated by focusing on a plurality of peaks of the relevant base type present near the peak, which is stored in the known information database 1d. For example, five peaks (peak numbers x1, x2, x3, x4, x5; 4b, 4c, 4d, 4e, 4f) of the base type in the neighborhood of the peak (peak number k; 4a) may be selected to calculate the average value and standard deviation in the data set for the five pieces of relative signal intensity $I_1, I_2, I_3, I_4, I_5$ given by the following formulae (2) to (6), which are then stored.

$$I_1 = I(k)/I(x1) \quad (2)$$

$$I_2 = I(x1)/I(x2) \quad (3)$$

$$I_3 = I(x1)/I(x3) \quad (4)$$

$$I_4 = I(x3)/I(x4) \tag{5}$$

$$I_2 = I(x4)/I(x5) \tag{6}$$

The combination of a plurality of pieces of relative signal intensity is not limited to the above example and other combinations may also be adopted.

Relative signal intensity information may be stored in the database 1d in FIG. 1 after, as described above, being acquired by the fluorescence intensity waveform data analyzer 1c in FIG. 1 or relative signal intensity information acquired by another apparatus may be stored in the database 1d in FIG. 1.

FIG. 6 shows an example of a table of relative signal intensity information when the relative signal intensity information calculated for the five pieces of relative intensity is stored. In this example, for each base type, the known base type (6b) and the average value and standard deviation of the calculated relative signal intensity (6c) for each coordinate position (6a) of the base sequence are stored in the table. For example, a table 601 concerning relative signal intensity of the base type A associates and stores, for each position 6a, the known base type 6b in the peak position when no polymorphism is contained (in position 99, for example, T is the known base sequence) and the relative signal intensity ($I_1$) of the base type A that is polymorphic in the position where the known base sequence is T. Further, calculation results of the formulae (3) to (6) like $I_2$ to $I_3$ are associated and stored. How to use the above information will be described below using FIG. 7.

An example of processing in which the fluorescence intensity waveform data analyzer 1c interprets fluorescence intensity waveform data newly obtained from a nucleic acid sample of the target gene to detect a gene mutation of some base type by referring to the relative signal intensity information (601 to 604) for reference obtained in the above procedure will be described below using FIG. 7.

In the processing in FIG. 7, the known base sequence and each peak of the new fluorescence intensity waveform data are associated (7a). For this purpose, a homology search of the known base sequence of the target gene stored in the database 1d in FIG. 1 and the base sequence of the new fluorescence intensity waveform data determined by performing the processing in FIG. 3 to associate the known base sequence and each peak of the new fluorescence intensity waveform data. Then, a neighboring peak of the relevant base type of the peak (peak number k) of the new fluorescence intensity waveform data is selected in some position (7b, 7c) and relative signal intensity $I_1$_new is calculated (7d). The calculation of the relative signal intensity $I_1$_new is similar to the processing of calculation of the relative signal intensity described above using 5d in FIG. 5 for the known base sequence. Other peaks to be selected may be other peaks than neighboring peaks and other preset peaks may be used for calculation or a plurality of pieces of relative signal intensity may be calculated by selecting a plurality of peaks of the relevant base type in the neighborhood of the relevant peak.

Next, the relative signal intensity in the relevant peak position in the aforementioned known base sequence in FIG. 6 is extracted from the database (7e) and any gene mutation in each peak position (peak number k) is detected based on the calculated relative signal intensity and the extracted relative signal intensity information (7f). The above processing is performed for each base type. In the same manner as the above series of procedures, any gene mutation is detected one after another for all positions (7g, 7h).

Any gene mutation is detected (7f) according to criteria of the following formulae (7), (8) after comparing the relative signal intensity calculated from the new fluorescence intensity waveform data with the relative signal intensity information obtained from the aforementioned fluorescence intensity waveform data set of the known base sequence in FIG. 6. For example, when the presence/absence of any mutation of the base type G is determined, a table 602 is referred to and for each position (6a), the known relative intensity ($I_1$) of the base type G and the relative signal intensity ($I_1$_new) of the base type G calculated from the new fluorescence intensity waveform data are compared according to the formulae (7), (8):

$$\{I_{1\_new} - Mean(I_1)\}/SD(I_1) \geq \text{threshold Mutation found} \tag{7}$$

$$\{I_{1\_new} - Mean(I_1)\}/SD(I_1) < \text{threshold No mutation} \tag{8}$$

Mean ($I_1$) is the average value of $I_1$ obtained from the fluorescence intensity waveform data of the known base sequence, SD($I_1$) is the standard deviation of $I_1$ obtained from the fluorescence intensity waveform data of the known base sequence, and threshold is a threshold set freely.

Any gene mutation can also be detected based on a plurality of pieces of relative signal intensity $I_1, I_2, \ldots, I_n$ according to criteria of the following formulae (10), (11) obtained by extending the above criteria multidimensionally:

$$\text{If set as } I = (I_1, I_2, \ldots, I_n)^T \tag{9}$$

$$(I\_new - \mu)^T S^{-1}(I\_new - \mu) \geq \text{threshold Mutation found} \tag{10}$$

$$(I\_new - \mu)^T S^{-1}(I\_new - \mu) < \text{threshold } No \text{ mutation} \tag{11}$$

μ is an average of I obtained from the fluorescence intensity waveform data of the known base sequence, S is a variance-covariance matrix of I obtained from the fluorescence intensity waveform data of the known base sequence, and threshold is a threshold set freely.

The above gene mutation detection processing can be performed independently of each base type. That is, for each base type, all positions can be examined for mutation.

Fluorescence intensity waveform data obtained by a DNA sequencer is characterized in that, though a relative magnitude of peak signal intensity exists even in one piece of waveform data, the magnitude depends on the gene sequence to be measured. That is, a relatively large peak in the same waveform data observed when a target gene made of the approximately the same gene sequence is analyzed is large regardless of trials and a small peak is small regardless of measurements. This feature is considered to be derived from the principle of the aforementioned DNA sequencing. In the nucleic acid fragmentation technology by the Sanger's method, as described above, nucleic acid is fragmented by dideoxynucleotide as chain termination nucleotide being incorporated. The tendency of deoxynucleotide and dideoxynucleotide being incorporated is mainly subject to a tertiary structure formed by template DNA and DNA synthetic enzyme and the tertiary structure is determined by the sequence of bases. Therefore, a nucleic acid fragment corresponding to coordinates where dideoxynucleotide is more likely to be incorporated is generated more and the signal intensity of the coordinates is always large. From the above, the relative magnitude of signal intensity of a peak in the fluorescence intensity waveform data can be considered to be determined mainly by the base sequence without depending on measurements. Therefore, the relative intensity of signal intensity of each peak normalized by signal intensity of neighboring peaks has a small variance between measurements. Accordingly, the mutation determination using relative intensity can make a sensitive determination.

A detection example of a trace gene mutation using a model sample according to the present embodiment will be described in more detail in combination with experiment content.

(Model Sample Adjustment)

As target genes for the model sample, the EGFR gene and the KRAS gene (base sequences thereof are known), which are cancer related genes and covered by insurance, are selected. Genome DNA extracted from human colon cancer cells (HCT116 p21(+)) is used as a template to amplify the EGFR gene and the KRAS gene by the PCR method and the genes are cloned in plasmid. DNA having a mutational gene sequence obtained by substituting the A base for the C base in 858 position of the EGFR gene and the T base for the C base in 12 position of the KRAS gene in an obtained wild type gene fragment is artificially produced and plasmid cloning is done in the same manner. QIAGEN Plasmid Plus Midi Kit is used to prepare plasmid DNA having each gene sequence. Wild type plasmid DNA and mutational plasmid DNA obtained as described above are mixed in the ratios of 100%: 0%, 99%:1%, 95%:5%, 90%:10%, 80%:20% to produce nucleic acid samples of different mutation ratios.

(Model Sample Measurement)

For measurements of fluorescence intensity waveform data used for evaluation of the present invention, eight label reactions are allowed for each ratio sample using ABI PRISM BigDye Primer v3.0 Ready Reaction Cycle Sequencing Kit For M13 REV Primers and the data is detected by 3130 Genetic Analyzer using an independent capillary for each base type. Accordingly, eight pieces of fluorescence intensity waveform data (EPF format data) are acquired for each base type of each abundance ratio.

(Fluorescence Intensity Waveform Data Processing)

The processing shown in FIG. 3 is performed on each piece of the obtained fluorescence intensity waveform data to detect a peak.

(Acquisition of Relative Signal Intensity Information)

For the base type A of the EGFR gene, eight pieces of fluorescence intensity waveform data in which the abundance ratio is 0% is used to select five peaks (peak numbers: x1, x2, x3, x4, x5; 3b, 3c, 3d, 3e, 3f) of the base type A in the neighborhood of a mutation position (peak number k; 3a) and the average value and standard deviation of the relative signal intensity $I_1, I_2, I_3, I_4, I_5$ of the formulae (2) to (6) are calculated and stored. Similarly, for the base type C of the EGFR gene, eight pieces of fluorescence intensity waveform data in which the abundance ratio is 100% is used to select five peaks of the base type C in the neighborhood of a mutation position and the average value and standard deviation of the relative signal intensity $I_1, I_2, I_3, I_4, I_5$ of the formulae (2) to (6) are calculated and stored.

Also, for the base type T of the KRAS gene, eight pieces of fluorescence intensity waveform data in which the abundance ratio is 0% is used to select five peaks of the base type T in the neighborhood of a mutation position and the average value and standard deviation of the relative signal intensity $I_1, I_2, I_3, I_4, I_5$ of the formulae (2) to (6) are calculated and stored.

Similarly, for the base type C of the KRAS gene, eight pieces of fluorescence intensity waveform data in which the abundance ratio is 100% is used to select five peaks of the base type C in the neighborhood of a mutation position and the average value and standard deviation of the relative signal intensity $I_1, I_2, I_3, I_4, I_5$ of the formulae (2) to (6) are calculated and stored.

(Mutation Detection)

For the base type A of the EGFR gene, any mutation in the fluorescence intensity waveform data in which the abundance ratio is 0%, 1%, 5%, 10%, 20% respectively is detected. First, five peaks of the base type A in the neighborhood of a mutation position are selected and the relative signal intensity $I_1\_new, I_2\_new, I_3\_new, I_4\_new, I_5\_new$ of the formulae (2) to (6) are calculated. Then, whether there is any mutation is determined according to the criteria of the formulae (7), (8) based on the relative signal intensity information of the base type A of the EGFR gene. In this case, threshold=3 is set. Further, whether there is any mutation is determined according to the criteria of the formulae (10), (11). In this case, threshold=16.75 is set. Similarly, for the base type C of the EGFR gene, any mutation in the fluorescence intensity waveform data in which the abundance ratio is 100%, 99%, 95%, 90%, 80% respectively is detected.

For the base type T of the KRAS gene, any mutation in the fluorescence intensity waveform data in which the abundance ratio is 0%, 1%, 5%, 10%, 20% respectively is detected. Similarly, for the base type C of the KRAS gene, any mutation in the fluorescence intensity waveform data in which the abundance ratio is 100%, 99%, 95%, 90%, 80% respectively is detected.

As a result, when the presence/absence of any mutation is determined according to the criteria of the formulae (7), (8), all data can be determined to have no mutation for the mutation abundance ratio of 0% and all data can be determined to have a mutation for the mutation abundance ratios of 5%, 10%, 20%. On the other hand, the detection rate decreases for the mutation abundance ratio of 1%. When the presence/absence of any mutation is determined according to the criteria of the formulae (10), (11), by contrast, all data can be determined to have no mutation for the mutation abundance ratio of 0% and all data can be determined to have a mutation for the mutation abundance ratios of 1%, 5%, 10%, 20%. The limit of mutation detection by conventional data analysis software is the mutation abundance ratio of about 30% and the limit of mutation detection is significantly improved by the present invention.

<Second Embodiment>

In the present embodiment, as a more concrete configuration example of the present embodiment that determines whether each base type in the base sequence coordinate position exists based on relative signal intensity information of signal intensity in each peak position relative to signal intensity in other peak positions, an example of analysis processing that detects the abundance ratio of each base type in each sequence coordinate position in fluorescence intensity waveform data performed by the fluorescence intensity waveform data analyzer 1c will be described using FIGS. 8, 9, 10, 11, and 12.

First, an example of processing that acquires relative signal intensity information for reference, that is, an example of processing that acquires relative signal intensity information from fluorescence intensity waveform data of the base type obtained for a known base sequence will be described using FIGS. 8 and 9.

Figure 8:
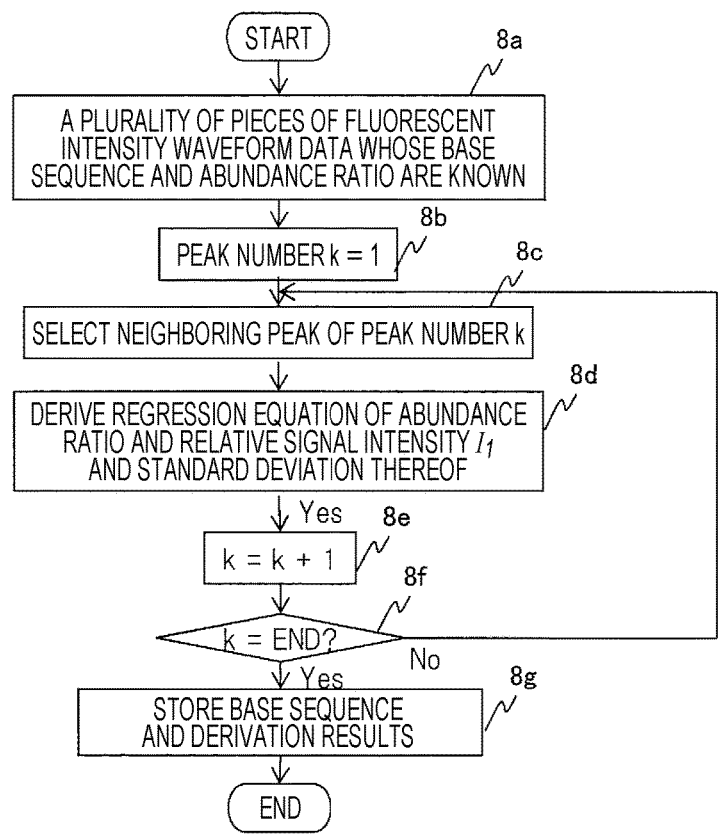
FIG. 8 shows a diagram showing an example of processing that acquires the relative signal intensity information to estimate a gene mutation abundance ratio.

In the processing in FIG. 8, a set of a plurality of pieces fluorescence intensity waveform data of some base type obtained for a known base sequence containing a mutation in a known abundance ratio is prepared (8a). Based on the data set, a peak that is a neighboring peak of a peak in some peak position is selected (8b, 8c). Next, a regression equation between the relative signal intensity $I_1$ of the signal intensity I(k) in the peak position relative to the signal intensity I(x1) in the neighboring peak position and the abundance ratio and a standard deviation thereof are derived (8d). The regression equation (formula 12) between the relative signal intensity $I_1$ and the abundance ratio R and the standard deviation (formula 13) thereof are calculated from the formula (14).

$$I_1 = a(R - \text{Mean}(R)) + \text{Mean}(I_1) \tag{12}$$

$$\sigma^2 = 1/(n-2)\Sigma(I_{1\_i} - I_1)^2 \tag{13}$$

$$a = \{\Sigma(R\_i - \text{Mean}(R))(I_{1\_i} - \text{Mean}(I_1))\}/\Sigma(R\_i - \text{Mean}(R))^2 \tag{14}$$

n is the number of pieces of fluorescence intensity waveform data of a known base sequence, $I_{1\_i}$ is $I_1$ of the i-th fluorescence intensity waveform data of the known base sequence, $\text{Mean}(I_1)$ is an average value of $I_1$ obtained from a fluorescence intensity waveform data set of the known base sequence, R_i is R of the i-th fluorescence intensity waveform data of the known base sequence, and Mean(R) is an average value of R obtained from the fluorescence intensity waveform data set of the known base sequence. In the same manner as the above series of procedures, the regression equation between the relative signal intensity $I_1$ and the abundance ratio and the standard deviation thereof are calculated one by one for all positions (8e, 8f) and the base sequence and calculation results are stored (8g). The same processing is repeated for all base types.

FIG. 11 shows an example of a table of relative signal intensity information when the regression equation derived for the relative intensity and the relative signal intensity information about the standard deviation thereof are stored. In this example, for each base type, the known base type (11b), an inclination a of the regression equation (formula (12)) between the derived relative intensity and the abundance ratio, an average value Mean(R) of the abundance ratio, an average value $\text{Mean}(I_1)$ of the relative intensity, the standard deviation (formula (13)) of the regression equation, and (11c) are stored in the table for each coordinate position (11a) of the base sequence. For example, a table 1101 concerning relative signal intensity of the base type A associates and stores, for each position 11a, the known base type 11b in the peak position when no polymorphism is contained (in position 99, for example, T is the known base sequence) and information about the regression equation between the relative signal intensity ($I_1$) and the abundance ratio and the standard deviation thereof of the base type A that is polymorphic in the position where the known base sequence is T. How to use the above information will be described below using FIG. 10.

Relative signal intensity information may be stored in the database 1d in FIG. 1 after being acquired by the fluorescence intensity waveform data analyzer 1c in FIG. 1 or relative signal intensity information acquired by another apparatus may be stored in the database 1d in FIG. 1.

An example of processing that interprets fluorescence intensity waveform data newly obtained from a nucleic acid sample of the target gene and estimates the abundance ratio of a gene mutation of some base type will be described below with reference to the regression equation between the relative signal intensity and the abundance ratio and the standard deviation thereof acquired according to the above procedure using FIG. 10.

Figure 10:
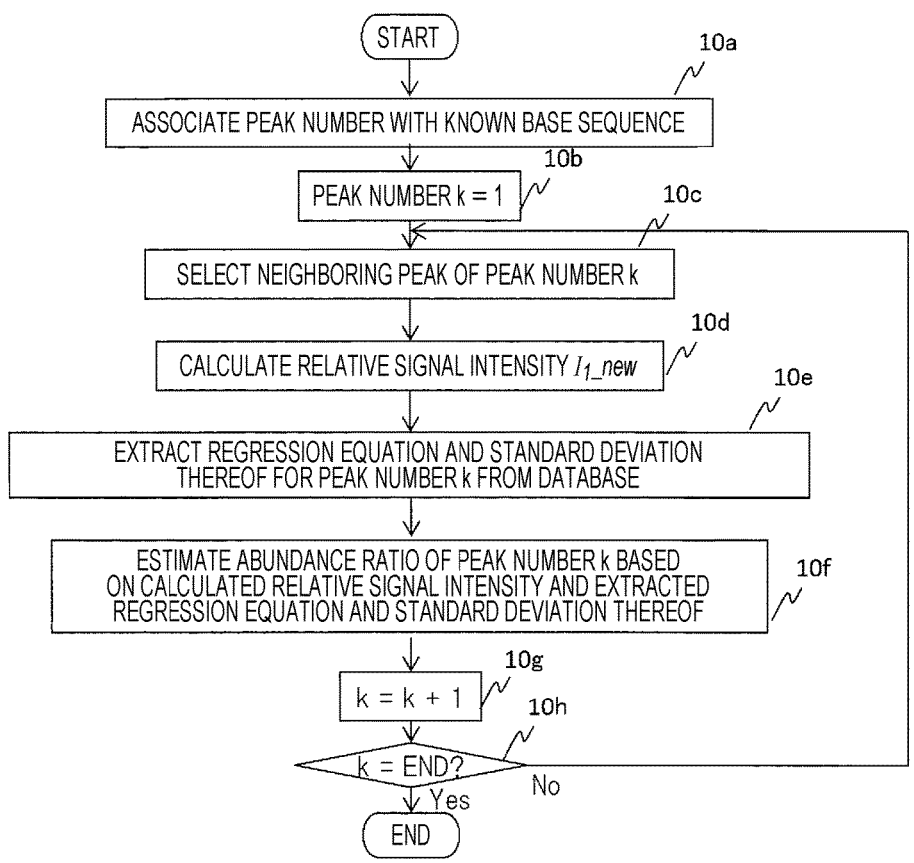
FIG. 10 is a diagram showing estimation processing of the gene mutation abundance ratio in the present invention.

In the processing in FIG. 10, the known base sequence and each peak of the new fluorescence intensity waveform data are associated (10a). For this purpose, a homology search of the known base sequence of the target gene stored in the database 1d in FIG. 1 and the base sequence of the new fluorescence intensity waveform data determined by performing the processing in FIG. 3 to associate the known base sequence and each peak of the new fluorescence intensity waveform data.

Then, a neighboring peak of the relevant base type of the peak (peak number k) of the new fluorescence intensity waveform data is selected in some position (10b, 10c) and relative signal intensity $I_1$_new is calculated (10d).

Next, information about the regression equation for the peak position and the standard deviation thereof are extracted from the database 1d (10e) and the abundance ratio of a gene mutation in each peak position is estimated based on the calculated relative signal intensity and the extracted information about the regression equation and the standard deviation thereof (10f). In the same manner as the above series of procedures, the abundance ratio of any gene mutation is estimated one after another for all positions (10g, 10h).

The abundance ratio of any gene mutation is estimated (10f) from the relative signal intensity calculated from new fluorescence intensity waveform data based on the aforementioned relative signal intensity information obtained from a fluorescence intensity waveform data set of a known base sequence in FIG. 11 according to the following formulae (15), (16). For example, when the mutation abundance ratio of the base type G is estimated, a table 1102 is referred to and the mutation abundance ratio is estimated from relative signal intensity ($I_1$_new) of the base type G calculated from new fluorescence intensity waveform data for each position (11a) based on information about the regression equation of the base type G and the standard deviation thereof according to the following formulae (15), (16).

$$R\_\text{new} = (I_{1\_\text{new}} - \text{Mean}(I_1))/a + \text{Mean}(R) \tag{15}$$

$$\sigma^2(R\_\text{new}) = \sigma^2/a^2 \tag{16}$$

FIG. 12 shows a display example when the mutation abundance ratio of each base type in each position obtained by the above method for a nucleic acid sample of the target gene. In this example, for each coordinate position of the base sequence, the known base type (12a) and the abundance ratios (12b, 12c, 12d, 12e) of all base types obtained in the position are displayed.

Heretofore, the case when the abundance ratio of a gene mutation has been described.

<Third Embodiment>

In the present embodiment, as an application example of the present embodiment that determines whether each base type exists in a base sequence coordinate position based on relative signal intensity information of the signal intensity in each peak position relative to the signal intensity in other peak positions, an application to the detection of a DNA methylation modification state will be described.

In the conventional detection of a DNA methylated gene, a general technique includes (i) conversion of cytosine C (non-methylated cytosine) that is not methylated in DNA into uracil U by the bisulfite process, (ii) gene amplification by PCR using a converted DNA sample as a template, (iii) plasmid cloning of gene amplification products, (iv) adjustment of about 100 clones of plasmid DNA, (v) fluorescence labeling reaction of about 100 clones, (vi) analysis of fluorescence labeling products by a DNA sequencer, (vii) calculation of the methylation rate by comparing the occurrence number of converted uracil U and the occurrence number of non-converted cytosine C based on the determined base sequence.

When the present invention enabling the detection of a gene mutation existing in trace amounts is applied to methylated gene detection, the process thereof includes (i) conversion of cytosine C (non-methylated cytosine) that is not methylated in DNA into uracil U by the bisulfite process, (ii) gene amplification by PCR using a converted DNA sample as a template, (iii) fluorescence labeling reaction of gene amplification products, (iv) analysis of fluorescence labeling products by a DNA sequencer, (v) calculation of the methylation rate by comparing the relative signal intensity derived from converted uracil U and the relative signal intensity derived from non-converted cytosine C. That is, the process taking cloning as an example can be shortened and the number of samples to be analyzed can be reduced from about 100 to one. A concrete embodiment will be described below.

First, the creation reference information by analyzing the target gene will be described. Reference fluorescence intensity waveform data is collected for both cases of the bisulfite process is performed and not performed on the target gene. When the bisulfite process is not performed, cytosine C in the sequence is all determined to be cytosine C. That is, cytosine C in the sequence becomes reference information when cytosine C is all methylated. When the bisulfite process is performed, cytosine C in the sequence is all determined to be uracil U and becomes reference information when none of cytosine C is methylated.

Next, the adjustment of a sample derived from a specimen will be described. After the bisulfite process being performed on a genome DNA sample from a specimen, a target gene region is amplified. The common PCR methods can be used as the gene amplification method, but it is desirable to consider the base sequence transformation by the bisulfite process for the primer design because non-methylated cytosine is converted into uracil.

Next, the detection of a methylated gene of a specimen will be described. As described in the first embodiment, relative signal intensity information in each position is acquired by the processing shown in FIG. 5 for all base types using reference fluorescence intensity waveform data. Then, the relative signal intensity in each position is calculated by the processing shown in FIG. 7 after specimen fluorescence intensity waveform data being input and the presence/absence of DNA methylation in each position is determined by detecting conversion from cytosine C to uracil U. Also, like in the second embodiment, the methylation rate can also be estimated from the abundance ratio thereof.

REFERENCE SIGNS LIST 1a, 1f Fluorescence intensity waveform data measuring unit
1b, 1g Control unit
1c Fluorescence intensity waveform data analyzer
1d Known information database
1e External network
1h Communication circuit
1x Gene mutation analyzer
2b Channel
2c Detector
601 Relative signal intensity information about the base type A
602 Relative signal intensity information about the base type G
603 Relative signal intensity information about the base type C
604 Relative signal intensity information about the base type T

The invention claimed is:

1. A gene mutation detecting method comprising:
(a) obtaining waveform data for each base type of a known base sequence, comprising:
(i) an average value (Mean($I_1$)) of relative signal intensity ($I_1$) at each peak position of the waveform data for each base type of the known base sequence, and
(ii) a standard deviation value (SD($I_1$)) of relative signal intensity ($I_1$) at each peak position of the waveform data for each base type of the known base sequence;
(b) performing electrophoresis of a nucleic acid sample to be analyzed for a gene mutation, wherein the nucleic acid sample to be analyzed is labeled for each base type or wherein the nucleic acid sample comprises a mixture of four types of fluorescent dyes;
(c) generating waveform data of detected intensity of the nucleic acid sample to be analyzed by detecting a label signal for each base type;
(d) detecting from the waveform data generated in step (c) at least one peak position for each base type;
(e) selecting from the waveform data generated in step (c) at least one neighboring peak position to each peak position of step (d) for each base type;
(f) calculating relative signal intensity ($I_1$_new) of signal intensity of each peak position of step (d) relative to signal intensity of the neighboring peak position of step (e); and
(g) comparing the results of step (a) with the results obtained from steps (b)-(f) using formulae (7) and (8) to determine the presence or absence of a gene mutation:

$$\{I_1\_\text{new}-\text{Mean}(I_1)\}/SD(I_1) \geq \text{threshold Mutation found} \quad (7)$$

$$\{I_1\_\text{new}-\text{Mean}(I_1)\}/SD(I_1) < \text{threshold No mutation} \quad (8),$$

wherein the threshold is freely set.

2. The method according to claim 1, wherein an abundance ratio of the base types on a same base row is calculated by comparing the relative signal intensity of the nucleic acid sample to be analyzed and the known relative signal intensity in each peak position.

3. The method according to claim 1, wherein the relative signal intensity is calculated by using at least a neighboring peak of the peak as the other peak.

4. The method according to claim 1, wherein a base sequence of the nucleic acid sample is determined based on an average value or a standard deviation of the relative signal intensity.

5. The method according to claim 1, wherein non-methylated cytosine C of the nucleic acid sample is converted into uracil U,
the relative signal intensity of the converted nucleic acid sample is calculated, and
whether DNA methylation is present is determined based on the calculated relative signal intensity.

* * * * *